US006368850B1

(12) United States Patent
Bernegger-Egli et al.

(10) Patent No.: US 6,368,850 B1
(45) Date of Patent: *Apr. 9, 2002

(54) PROCESS FOR THE PREPARATION OF AMINO ALCOHOLS AND DERIVATIVES THEREOF

(75) Inventors: Christine Bernegger-Egli, Münster; Olwen M. Birch, Visp; Pierre Bossard, Onex; Walter Brieden, Glis; Frank Brux, Raron; Knut Burgdorf, Ried-Brig; Laurent Duc, Chermignon; Kay-Sarah Etter, Niedergampel; Yves Guggisberg, Sierre; Martin Sauter; Eva Maria Urban, both of Visp, all of (CH)

(73) Assignee: Lonza AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/194,626

(22) PCT Filed: May 30, 1997

(86) PCT No.: PCT/EP97/02838

§ 371 Date: May 21, 1999

§ 102(e) Date: May 21, 1999

(87) PCT Pub. No.: WO97/45529

PCT Pub. Date: Dec. 4, 1997

(30) Foreign Application Priority Data

May 30, 1996 (CH) .............................................. 1359/96
Feb. 10, 1997 (CH) .............................................. 0282/97
Apr. 18, 1997 (CH) .............................................. 908/97

(51) Int. Cl.$^7$ .............................................. C12P 41/00
(52) U.S. Cl. .................................................... 435/280
(58) Field of Search ........................................ 435/280

(56) References Cited

FOREIGN PATENT DOCUMENTS

| WO | WO9101318 | 2/1991 |
| WO | WO9101319 | 2/1991 |
| WO | WO9115447 | 10/1991 |
| WO | WO9317020 | 9/1993 |

OTHER PUBLICATIONS

Martinez et al., 1996, "Highly efficient and enantioselective synthesis of carbocylic nucleoside analogs using selective early transition metal catalysis", *J. Org. Chem*.61:7963–7966.
Campbell et al., 1995, Chirospecific synthesis of precursors of cyclopentane carbocyclic nucleosides by [3+3]–coupling and transannular alkylation, *J. Org. Chem*. 60:4602–4616.
Park et al., 1994, "Enantioselective synthesis of (1R, 4S)–1–amino–4–(hydroxymethyl)–2–cyclopentane, a precursor for carbocyclic nucleoside synthesis", *J. Org. Chem*. 59:394–399.

Taylor, et al., 1993, Development of the biocatalytic resolution of 2–azabicyclo[2.2.1]hept–5–en–3–one as an entry to single enantiomer carbocyclic nucleosides, *Tetrahedron: Asymmetry* 4: 1117–1128.

Norman et al., 1992, "Novel synthesis of (+/−)–cis–4–amino–2–cyclopentene–1–methanol, a key intermediate in the preparation of carbocyclic 2',3'–didehydro–2', 3'–dideoxy nucleosides", *Synthetic Communications* 22, 3197–3204.

*Primary Examiner*—Sandra E. Saucier

(57) ABSTRACT

The invention relates to a novel process for the preparation of (1R,4S)- or (1S,4R)-1-amino-4-(hydroxymethyl)-2-cyclopentene of the formulae

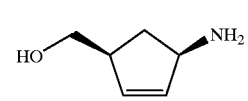

I

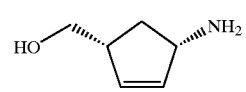

II and/or of (1S,4R)- or (1R,4S)-amino alcohol derivatives of the general formulae

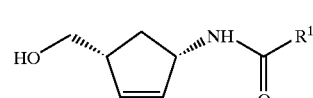

III

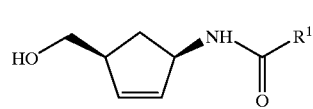

IV and to novel microorganisms which are able to utilize a cyclopentene derivative of the general formula

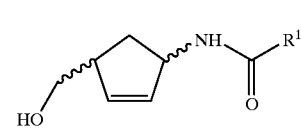

VII as sole nitrogen source, as sole carbon source or as sole carbon and nitrogen source.

The invention further relates to enzyme extracts and enzymes having N-acetylamino-alcohol hydrolase activity obtainable from these microorganisms.

13 Claims, 2 Drawing Sheets

SEQUENCE LISTING

<160> NUMBER OF SEQ ID NOS: 1

<210> SEQ ID NO 1
<211> LENGTH: 20
<212> TYPE: PRT
<213> ORGANISM: Rhodococcus erythropolis

<400> SEQUENCE: 1

Thr Glu Gln Asn Leu His Trp Leu Ser Ala Thr Glu Met Ala Ala Ser
1               5                   10                  15

Val Ala Ser Asn
            20

PROCESS FOR THE PREPARATION OF AMINO ALCOHOLS AND DERIVATIVES THEREOF

The invention relates to a novel process for the preparation of (1R,4S)- or (1S,4R)-1-amino-4-(hydroxymethyl)-2-cyclopentene of the formulae

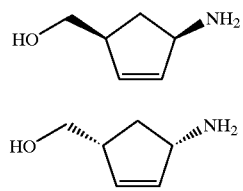

I

II and/or of (1S,4R)- or (1R4S)-amino alcohol derivatives of the general formulae

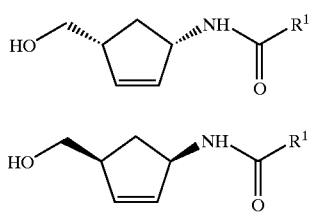

III

IV and to novel microorganisms which are able to utilize a cyclopentene derivative of the general formula

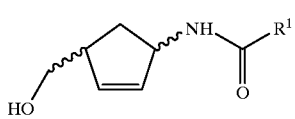

VII as sole nitrogen source, as sole carbon source or as sole carbon and nitrogen source.

The invention further relates to enzyme extracts and enzymes having N-acetylamino-alcohol hydrolase activity obtainable from these microorganisms.

BACKGROUND OF THE INVENTION (1R,4S)-1-Amino-4-(hydroxymethyl)-2-cyclopentene of the formula I is an important intermediate for the preparation of carbocyclic nucleosides such as, for example, Carbovir® (Campbell et al., J. Org. Chem. 1995, 60, 4602–4616).

Processes for the preparation of (1R,4S)-1-amino-4-(hydroxymethyl)-2-cyclopentene are described by Campbell et al. (ibid) and by Park K. 11. & Rapoport H. (J. Org. Chem. 1994, 59, 394–399).

The precursor used in these processes is either D-glucono-δ-lactone or D-serine, and about 15 synthesis stages are necessary to form (1R,4S)-N-tert-butoxycarbonyl-4-hydroxymethyl-2-cyclopentene, which is then deprotected to give (1R,4S)-1-amino-4-(hydroxymethyl)-2-cyclopentene. These two processes are costly, elaborate and cannot be implemented industrially.

WO 93/17020 describes a process for the preparation of (1R,4S)-1-amino-4-(hydroxymethyl)-2-cyclopentene, wherein (1R,4S)-4-amino-2-cyclopentene-1-carboxylic acid is reduced with lithium aluminium hydride to the desired product.

The disadvantage of this process is, on the one hand, that the double bond of the cyclopentene ring is also reduced, the lithium aluminium hydride is difficult to handle, and, on the other hand, that it is too costly.

Taylor, S. J. et al. (Tetrahedron: Asymmetry Vol. 4, No. 6, 1993, 1117–1128) describe a process for the preparation of (1R,4S)-1-amino-4-(hydroxymethyl)-2-cyclopentene starting from (±)-2-azabicyclo[2.2.1]hept-5-en-3-one as precursor. In this case, the precursor is converted by means of microorganisms of the species *Pseudomonas solanacearum* or *Pseudomonas fluorescens* into (1R, 4S)-2-azabicyclo[2.2.1]hept-5-en-3-one, which is then converted with di-tert-butyl dicarbonate into (1R,4S)-N-tert-butoxycarbonyl-2-azabicyclo[2.2.1]hept-5-en-3-one, which is reduced with sodium borohydride and trifluoroacetic acid to the desired product. This process is much too costly.

In addition, Martinez et al. (J. Org. Chem. 1996, 61, 7963–7966) describe a 10-stage synthesis of (1R,4S)-1-amino-4-(hydroxymethyl)-2-cyclopentene starting from diethyl dialkylmalonate. This process also has the disadvantage that it is elaborate and cannot be implemented industrially.

SUMMARY OF THE INVENTION

It was an object of the present invention to provide a simple process for the preparation of (1R,4S)-1-amino-4-(hydroxymethyl)-2-cyclopentene.

This object is achieved with the microorganisms of the invention according to claim 1, and enzyme extracts therefrom, with the enzymes of the invention according to claim 4 and with the process of the invention according to claim 7.

DETAILED DESCRIPTION OF THE INVENTION

Figure 1:
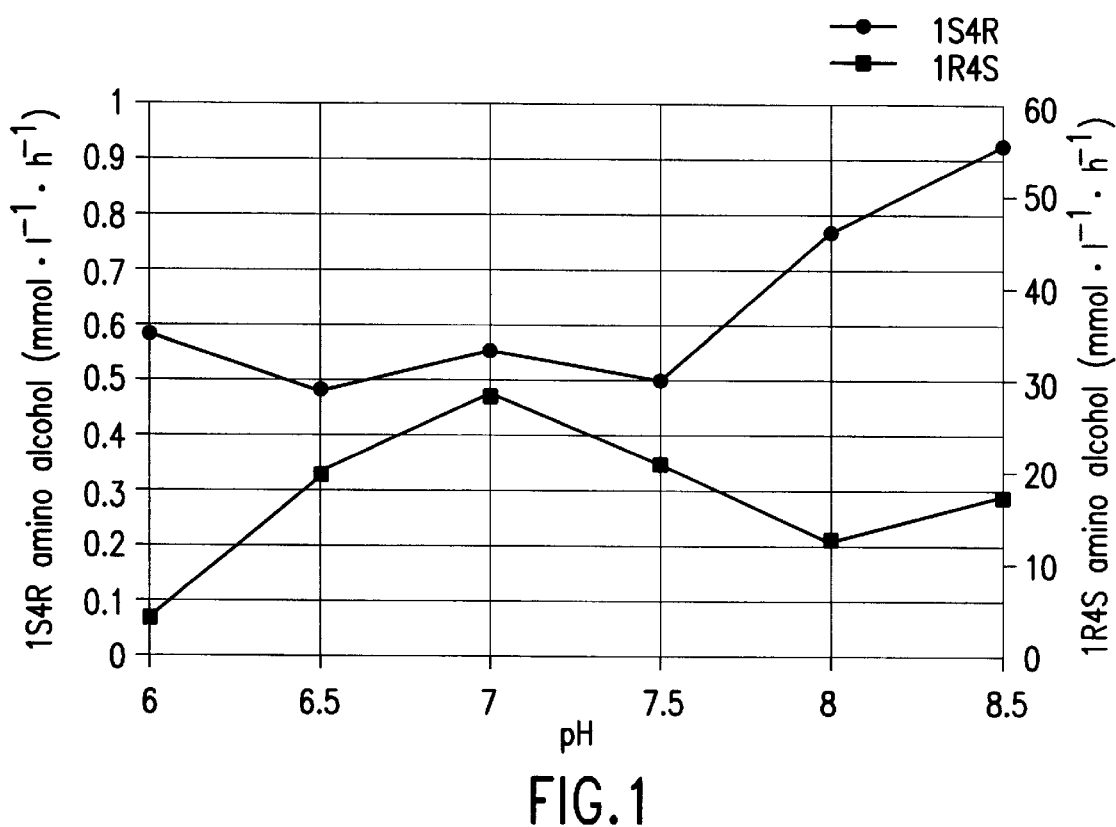
FIG. 1 shows the activity of the N-acetylaminoalcohol hydrolase (cell-free extract) from *Rhodococcus crythropolis* CB 101 (DSM 10686) as a function of the pH.
16.3 The temperature optimum for the reaction indicated in Example 16.2 was between 25 and 30° C.
Figure 2:
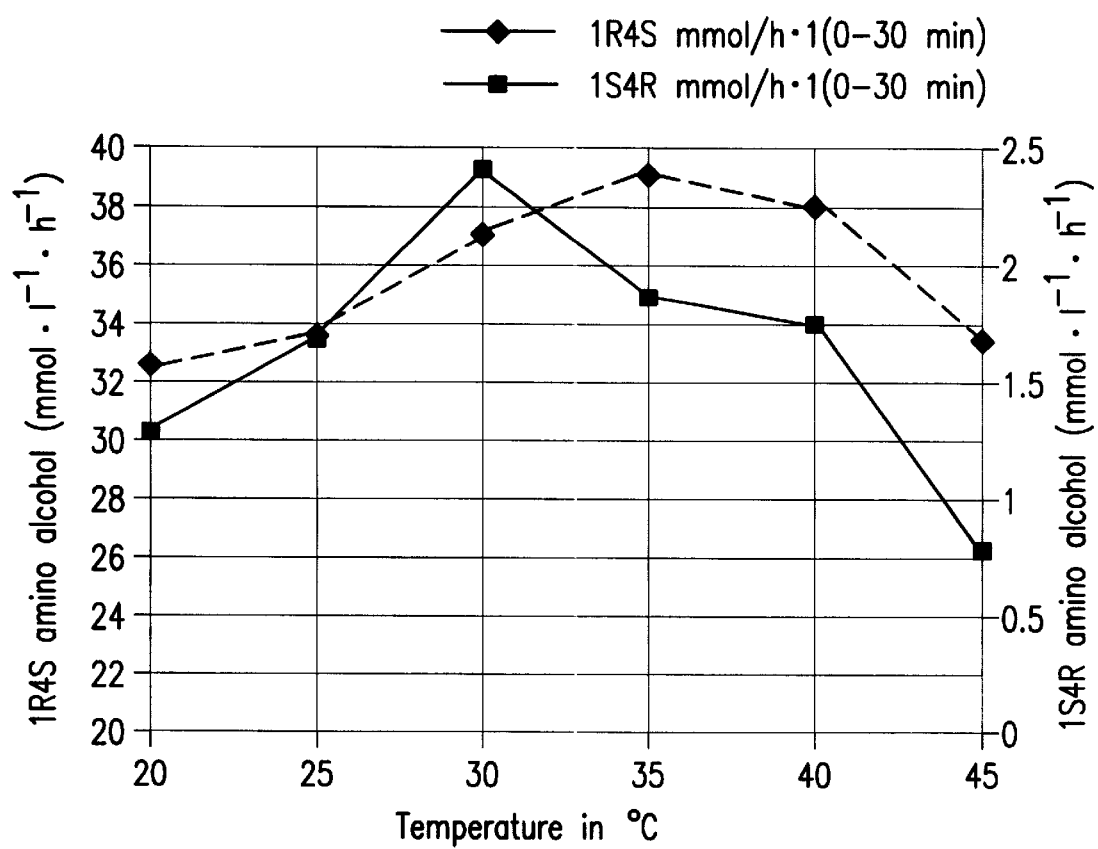
FIG. 2 shows the activity of the N-acctylaminoalcohol hydrolase (cell-free extract) from *Rhodococcus erythropolis* CB 101 (DSM 10686) as a function of the temperature.

The microorganisms of the invention can be isolated from soil samples, sludge or wastewater with the assistance of conventional microbiological techniques.

The microorganisms are isolated according to the invention by cultivating them in a nutrient medium containing one or more cyclopentene derivatives of the general formula

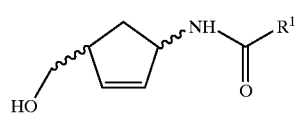

VII in which $R^1$ denotes $C_1$–$C_4$-alkyl, $C_1$–$C_4$-alkoxy, aryl or aryloxy,
   as sole carbon and nitrogen source
   as sole nitrogen source with a suitable carbon source or
   as sole carbon source with a suitable nitrogen source, in a conventional way.

It is possible to use as $C_1$–$C_4$-alkyl for example methyl, ethyl, propyl, isopropyl or butyl. It is possible to use as $C_1$–$C_4$-alkoxy for example methoxy, ethoxy, propoxy, isopropoxy, butoxy or tert-butoxy. It is possible to use as aryl for example phenyl or benzyl. Benzyl is preferably used. It is possible to use as aryloxy for example benzyloxy or phenoxy. Accordingly, the following examples are suitable as cyclopentene derivative of the general formula VII:
1-acetylamino-4-hydroxymethyl-2-cyclopentene, 1-butyrylamino-4-hydroxymethyl-2-cyclopentene or 1-phenylacetylamino-4-hydroxymethyl-2-cyclopentene.

It is expedient to select from the culture obtained by cultivation those which utilize the (1R,4S) isomer of the cyclopentene derivative of the formula VII as sole nitrogen source, as sole carbon source or as sole carbon and nitrogen source.

The microorganisms can use as suitable nitrogen source for example, ammonium, nitrates, amino acids or ureas as substrate for growth. The microorganisms can use as suitable carbon source, for example, sugars, sugar alcohols, $C_2$–$C_4$-carboxylic acids or amino acids as substrate for growth. Hexoses such as glucose or pentoses can be used as sugars. Glycerol, for example, can be used as sugar alcohol. Acetic acid or propionic acid can be used, for example, as $C_2$–$C_4$-carboxylic acids. Leucine, alanine, asparagine can be used, for example, as amino acids.

The selection medium and culture medium which can be used are those conventional among those skilled in the art, such as, for example, the one described in Table 1 or a complete medium (medium containing yeast extract), preferably using the one described in Table 1.

During the culturing and selection, the active enzymes of the microorganisms are expediently induced. The cyclopentene derivatives of the general formula VII can be used as enzyme inducer.

The culturing and selection normally takes place at a temperature from 20° C. to 40° C., preferably from 30° C. to 38° C. and at a pH between 5.5 and 8.0, preferably between 6.8 and 7.8.

Preferred microorganisms are those of the genus Rhodococcus, Gordona, Arthrobacter, Alcaligenes, Agrobacterium/Rhizobium, Bacillus, Pseudomonas or Alcaligenes/Bordetella, in particular of the species *Rhodococcus erythropolis* CB 101 (DSM 10686), Alcaligenes/Bordetella FB 188 (DSM 11172), Arthrobacter sp. HSZ 5 (DSM 10328), Rhodococcus sp. FB 387 (DSM 11291), *Alcaligenes xylosoxydans* ssp. denitrificans HSZ 17 (DSM 10329), Agrobacterium/Rhizobium HSZ 30, *Bacillus simplex* K2, *Pseudomonas putida* K32, or Gordona sp. CB 100 (DSM 10687) and their functionally equivalent variants and mutants. Deposition in accordance with the Budapest Treaty at the Deutsche Sammlung von Mikro-organismen and Zellkulturen GmbH (DSMZ), Mascheroderweg lb, D-38124 Braunschweig, took place on 20.05.1996 for the microorganisms DSM 10686 and 10687, on 6.11.1995 for the microorganisms DSM 10328 and DSM 10329, on 8.10.1996 for the microorganism DSM 11291 and on 20.09.1996 for the microorganism DSM 11172.

"Functionally equivalent variants and mutants" mean microorganisms having essentially the same properties and functions as the original microorganisms. Variants and mutants of this type can be produced by chance, for example by UV radiation.

| Taxonomic description of Alcaligenes/Bordetella FB 188 (DSM 11172) | |
|---|---|
| Cell form | rods |
| Width μm | 0.5–0.6 |
| Length μm | 1.0–2.5 |
| Motility | + |
| Flagellation | peritrichous |
| Gram reaction | – |
| Lysis by 3% KOH | + |
| Aminopeptidase (Cerny) | + |
| Spores | – |
| Oxidase | + |
| Catalase | + |
| ADH (alcohol dehydrogenase) | – |
| $NO_2$ from $NO_3$ | – |
| Denitrification | – |
| Urease | – |
| Hydrolysis of gelatin | – |
| Acid from (OF test): | |
| Glucose | – |
| Fructose | – |
| Arabinose | – |
| Adipate | + |
| Caprate | + |
| Citrate | + |
| Malate | + |
| Mannitol | – |

Taxonomic Description of *Rhodococcus Erythropolis* CB 101 (DSM 106 86)
1. Morphology and color of the colonies: short branched hyphae which, when old, disintegrate into rods and cocci, colonies glistening and partly confluent, beige with pink tinge, RAL 1001;
2. Diagnosed amino acid of the peptidoglycan: meso-diaminopimelic acid;
3. Mycolic acids: Rhodococcus mycolic acids; determination of the mycolic acid chain length ($C_{32}$–$C_{44}$) and comparison of the data with the entries in the DSM mycolic acid data bank revealed very great similarity with the patterns of the Rhodococcus erythropolis strains (similarity 0.588);
4. Fatty acid pattern: unbranched, saturated and unsaturated fatty acids plus tuberculostearic acid
5. On partial sequencing of the 16S rDNA of the strain, a high level of agreement (1000) was found with the sequences of the specific regions of *Rhodococcus erythropolis*.

The identification result is unambiguous because three mutually independent methods (mycolic acids, fatty acids, 16S rDNA) have assigned the strain to the species *Rhodococcus erythropolis*.

Taxonomic description of Gordona sp. CB 100 (DSM 10687)
1. Morphology and color of the colonies: short branched hyphae which, when old, disintegrate into rods and cocci, colonies pale orange, (RAL 2008);
2. Diagnosed amino acid of the peptidoglycan: meso-diaminopimelic acid;
3. Menaquinone pattern: MK-9 ($H_2$) 100%;
4. Mycolic acids: Gordona mycolic acids; the mycolic acid chain length ($C_{50}$–$C_{60}$) was determined by high temperature gas chromatography. This pattern corresponds to the pattern found in representatives of the genus Gordona.
5. Fatty acid pattern: unbranched, saturated and unsaturated fatty acids plus tuberculostearic acid;

6. On partial sequencing of the 16S rDNA of the strain, only a relatively low agreement of 98.8% could be found with the sequences of the specific regions of Gordona rubropertincta.

On the basis of the available results (menaquinones, mycolic acids, fatty acids, 16S rDNA), although the isolate can be unambiguously assigned to the genus Gordona it is not possible on the basis of the results to make an assignment to a known Gordona species. It is therefore to be assumed that the strain DSM 10687 is a new and previously undescribed species of the genus Gordona.

| Taxonomic description of Alcaligenes xylosoxydans ssp. denitrificans HSZ 17 (DSM 10329) | |
|---|---|
| Properties of the strain | |
| Cell form | rods |
| Width $\mu$m | 0.5–0.6 |
| Length $\mu$m | 1.5–3.0 |
| Motility | + |
| Flagellation | peritrichous |
| Gram reaction | − |
| Lysis by 3% KOH | + |
| Aminopeptidase (Cerny) | + |
| Spores | − |
| Oxidase | + |
| Catalase | + |
| Anaerobic growth | − |
| ADH (alcohol dehydrogenase) | + |
| $NO_2$ from $NO_3$ | + |
| Denitrification | + |
| Urease | − |
| Hydrolysis of Gelatin | − |
| Tween 80 | − |
| Acid from (OF test): | |
| Glucose aerobic | − |
| Xylose 80 | − |
| Substrate utilization | |
| Glucose | − |
| Fructose | − |
| Arabinose | − |
| Citrate | + |
| Malate | + |
| Mannitol | − |

| Taxonomic description of Axthrobacter sp. HSZ5 (DSM 10328) | |
|---|---|
| Characterization: | Gram-positive irregular rods with a pronounced rod-cocci growth cycle; strictly aerobic; no acid or gas formation from glucose. |
| Motility | − |
| Spores | − |
| Catalase | + | meso-Diaminopimelic acid in the cell wall: no

Peptidoglkycan type: A3cx, L-Lys-L-Ser-L-Thr-L-Ala 16S rDNA sequence similarity: The highest values found on sequencing the region with the greatest variability were 98.2% with *Arthrobacter pascens, A. ramosus* and *A. oxydans*.

| Taxonomic description of Agrobacterium/Rhizobium HSZ30 | |
|---|---|
| Cell form | pleomorphic rods |
| Width [$\mu$m] | 0.6–1.0 |
| Length [$\mu$m] | 1.5–3.0 |
| Gram reaction | − |
| Lysis by 3% KOH | + |
| Aminopeptidase | + |
| Spores | − |
| Oxidase | + |
| Catalase | + |
| Motility | + |
| Anaerobic growth | − |
| Nitrite from nitrate | − |
| Denitrification | − |
| Urease | + |
| Hydrolysis of gelatin | − |
| Acid from: | |
| L-Arabinose | + |
| Galactose | − |
| Melezitose | − |
| Fucose | + |
| Arabitol | − |
| Mannitol | − |
| Erythritol | − |
| Alkalinization of litmus milk | + |
| Ketolactose | − |

Partial sequencing of the 16S rDNA revealed comparably large similarities of about 96% with representatives of the genera Agrobacterium and Rhizobium. Unambiguous assignment to a species described within these genera is not possible.

| Taxonomic description of Bacillus simplex K2 | |
|---|---|
| Cell form | rods |
| Width [$\mu$m] | 0.8–1.0 |
| Length [$\mu$m] | 3.0–5.0 |
| Spores | − |
| Ellipsoidal | − |
| Circular | − |
| Sporangium | − |
| Catalase | + |
| Anaerobic growth | − |
| VP reaction | n.g. |
| Maximum temperature | |
| Growth positive at ° C. | 40 |
| Growth negative at ° C. | 45 |
| Growth in medium pH 5.7 | − |
| NaCl | |
| 2% | + |
| 5% | − |
| 7% | − |
| 10% | − |
| Lysozyme medium | + |
| Acid from (ASS) | |
| D-Glucose | + |
| L-Arabinose | + |
| D-Xylose | − |
| D-Mannitol | + |
| D-Fructose | + |
| Gas from fructose | − |
| Lecithinase | − |
| Hydrolysis of Starch | + |
| Gelatin | + |
| Casein | − |
| Tween 80 | + |
| Aesculin | − |
| Utilization of Citrate | + |

-continued

| Taxonomic description of Bacillus simplex K2 | |
|---|---|
| Propionate | − |
| Nitrite from nitrate | + |
| Indole | − |
| Phenylalanine deaminase | − |
| Arginine dihydrolase | − |

Analysis of the cellular fatty acids yielded confirmation of the assignment to the genus Bacillus.

Partial sequencing of the 16S rDNA revealed a similarity of 100% with *Bacillus simplex*.

| Taxonomic description of *Pseudomonas putida* K32 | |
|---|---|
| Cell form | rods |
| Width [μm] | 0.8–0.9 |
| Length [μm] | 1.5–4.0 |
| Motility | + |
| Flagellation | polar > 1 |
| Gram reaction | − |
| Lysis by 3% KOH | + |
| Aminopeptidase | + |
| Spores | − |
| Oxidase | + |
| Catalase | + |
| Anaerobic growth | − |
| Pigments | |
| fluorescent | + |
| Pyocyanin | − |
| ADH | + |
| Nitrite from nitrate | − |
| Denitrification | − |
| Urease | − |
| Hydrolysis of gelatin | − |
| Substrate utilization | |
| Adipate | − |
| Citrate | + |
| Malate | + |
| D-Mandelate | + |
| Phenylacetate | + |
| D-Tartrate | − |
| D-Glucose | + |
| Trehalose | − |
| Mannitol | − |
| Benzoylformate | − |
| Propylene glycol | + |
| Butylamine | + |
| Benzylamine | + |
| Tryptamine | − |
| Acetamide | + |
| Hippurate | + |

The profile of cellular fatty acids is typical of *Pseudomonas putida*.

Partial sequencing of the 16S rDNA revealed similarities of about 98% with *Pseudomonas mendocina* and *Pseudomonas alcaligenes*. The similarity with *Pseudomonas putida* was 97.4%.

Taxonomic Description of Rhodococcus sp. FB 387 (DSM 11291)

1. Morphology and colour of the colonies: short branched hyphae which, when old, disintegrate to rods and cocci, colonies matt, pale red-orange RAL 2008;
2. Diagnosed amino acid of the peptidoglycan: meso-diaminopimelic acid;
3. Mycolic acids: Rhodococcus mycolic acids; Determination of the mycolic acid chain length ($C_{32}$–$C_{44}$) and comparison of the data with the entries in the DSM7 mycolic acid data bank revealed only very small similarity with the patterns of Rhodococcus ruber strains (similarity 0.019). This correlation factor is too low to be used for species identification;
4. Fatty acid pattern: unbranched, saturated and unsaturated fatty acids plus tuberculostearic acid. This fatty acid pattern is diagnostic for all representatives of the genus Rhodococcus and its close relatives such as Mycobacterium, Nocardia and Gordona. An attempt was made by including the qualitative and quantitative differences in the fatty acid pattern to carry out a differentiation to the species level. Numerical methods were used to compare the fatty acid pattern of Rhodococcus sp. FB 387 with the entries in the data bank. It was not possible with this method either to assign Rhodococcus sp. FB 387, because of the small similarity (0.063), to any described Rhodococcus species;
5. On partial sequencing of the 16S rDNA of the strain, 96–818 was assigned to *Rhodococcus opacus* with a correlation of 97.9%. This sequence agreement is far below that of 99.5% required for unambiguous species assignment in this taxon.

On the basis of the available results, it can be assumed that the strain Rhodococcus sp. FB 387 is a new and not previously described Rhodococcus species.

The enzymes of the invention, the N-acetylamino-alcohol hydrolases which are able to hydrolyse cyclopentene derivatives of the above formula VII, can be obtained, for example, by disruption of the microorganism cells of the invention in a way conventional for the skilled person. It is possible to use for this for example the ultrasound or French press method. These enzymes can be obtained for example from *Rhodococcus erythropolis* C13 101 (DSM 10686) microorganisms. Enzymes obtainable from the microorganisms of the invention, especially *Rhodococcus erythropolis* CB 101 (DSM 10686), preferably have the following properties:

a) a pH optimum of pH 7.0±1.0;

b) a temperature optimum between 25° and 30° C. at a pH of 7.0; and c) a KM for the substrate 1-acetylamino-hydroxymethyl-2-cyclopentene of 22.5 mM±7.5 mM (30° C., 100 mM phosphate buffer, pH 7.0).

Sequence analysis of an enzyme obtainable from *Rhodococcus erythropolis* CB 101 (DSM 10686) further revealed:

d) an N-terminal amino acid sequence of Thr-Glu-Gln-Asn-Leu-His-Trp-Leu-Ser-Ala-Thr-Glu-Met-Ala-Ala-Ser-Val-Ala-Ser-Asn; and a molecular weight determination revealed:

e) a molecular weight of 50 kD determined by SDS-PAGE.

Enzymes like those obtainable from the microorganisms of the invention, for example *Rhodococcus erythropolis* CB 101 (DSM 10686), hydrolyse, for example, in particular 1-acetylamino-4-hydroxymethyl-2-cyclopentene, 1-butyrylamino-4-hydroxymethyl-2-cyclopentene, 1-propionylamino-4-hydroxymethyl-2-cyclopentene and 1-isobutyrylamino-4-hydroxymethyl-2-cyclopentene.

The process of the invention for the preparation of (1R,4S)- or (1S,4R)-1-amino-4-(hydroxymethyl)-2-cyclopentene of the formulae

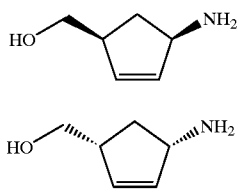

I

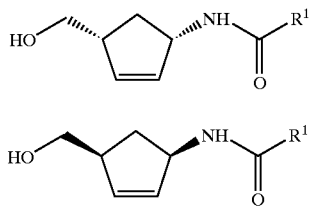

II and/or of (1S, 4R)- or (1R, 4S)- amino alcohol derivatives of the general formulae

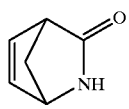

III

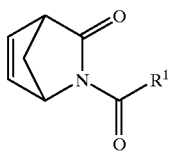

IV in which R¹ has the stated meaning, can be carried out for example by, in a first stage, acylating (±)-2-azabicyclo[2.2.1]hept-5-en-3-one of the formula

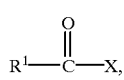

V to give a (±)-2-azabicyclo[2.2.1]hept-5-en-3-one derivative of the general formula

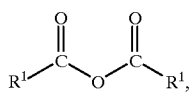

VI in which R¹ has the stated meaning.

The precursor (±)-2-azabicyclo[2.2.1]hept-5-en-3-one can be prepared as disclosed in EP-B 0 508 352.

The acylation can be carried out with a carbonyl halide of the general formula

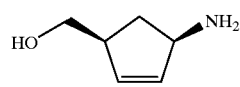

VIII in which X denotes a halogen atom, and R¹ has the stated meaning, or with a carboxylic anhydride of the general formula

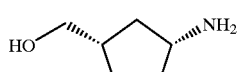

IX in which R¹ has the stated meaning.

F, Cl, Br or I can be used as halogen atom X. Cl or F is preferably used.

Examples of carbonyl halides are: acetyl chloride, chloroacetyl chloride, butyryl chloride, isobutyryl chloride, phenylacetyl chloride, benzyl chloroformate (Cbz-Cl), propionyl chloride, benzoyl chloride, allyl chloroformate or tert-butyl fluoroformate. Examples of carboxylic anhydrides are: di-tert-butyl dicarbonate, butyric anhydride, acetic anhydride or propionic anhydride.

The acylation can be carried out without solvent or with an aprotic solvent.

The acylation is expediently carried out in an aprotic solvent. Examples of suitable aprotic solvents are pyridine, acetonitrile, dimethylformamide, tetrahydrofuran, toluene, methylene chloride, N-methylpyrrolidone or mixtures thereof. The solvent preferably used is pyridine or acetonitrile, in particular a mixture of pyridine and acetonitrile.

The acylation is expediently carried out at a temperature from −80 to 50° C., preferably from 0 to 25° C.

In a second stage of the process, the (±)-2-azabicyclo[2.2.1]hept-5-en-3-one derivative of the formula VI can be reduced to give a cyclopentene derivative of the general formula

VII in which R¹ has the stated meaning.

The reduction is expediently carried out with an alkali metal borohydride or alkaline earth metal borohydride, with an alkali metal aluminium hydride or alkaline earth metal aluminium hydride or with Vitride (sodium bis(2-methoxyethoxy)aluminium hydride). Sodium or potassium aluminium hydride can be used as alkali metal aluminium hydride. Sodium or potassium borohydride can be used as alkali metal borohydride. Calcium borohydride can be used as alkaline earth metal borohydride.

The reduction is expediently carried out in a protic solvent. Protic solvents which can be used are lower aliphatic alcohols such as methanol, ethanol, propanol, isopropanol, butanol, isobutanol, sec-butanol, tert-butanol, or water, or mixtures thereof.

The reduction is expediently carried out at a temperature from −40 to 40° C., preferably from 0 to 20° C.

The conversion of the cyclopentene derivative of the general formula VII into the (1R,4S)- or (1S,4R)-1-amino-4-(hydroxymethyl)-2-cyclopentene of the formulae

I

II is carried out according to the invention either by means of microorganisms or enzyme extracts therefrom, by means of penicillin G acylases or by means of enzymes having N-acetylamino-alcohol hydrolase activity. This biotransformation results not only in the (1R,4S)- or (1S,4R)-1-amino- 4-(hydroxymethyl)-2-cyclopentene of formula I or II, which is isolated where appropriate, but also in the (1S,4R)- or (1R,4S)-amino alcohol derivative of the general formulae

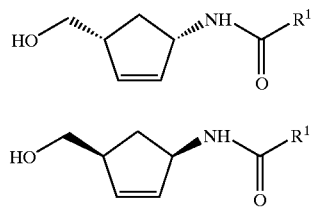

III

IV in which $R^1$ has the stated meaning. The latter can like-wise be isolated where appropriate.

All microorganisms which utilize a cyclopentene derivative of the general formula VII as sole nitrogen source, as sole carbon source or as sole carbon and nitrogen source are suitable. The biotransformation is expediently carried out with microorganisms which utilize the (1R,4S) isomer of the cyclopentene derivative as sole carbon source, as sole carbon and nitrogen source or as sole nitrogen source.

The biotransformation is preferably carried out by means of microorganisms of the genus Alcaligenes/Bordetella, Rhodococcus, Arthrobacter, Alcaligenes, Agrobacterium/Rhizobium, Bacillus, Pseudomonas or Gordona, in particular of the species Algaligenes/Bordetella FB 188 (DSM 11172), *Rhodococcus erythropolis* CB 101 (DSM 10686), Arthrobacter sp. HSZ 5 (DSM 10328), Rhodococcus sp FP 387 (DSM 11291), *Alcaligenes xylos-oxydans* ssp. denitrificans HSZ 17 (DSM 10329), Agrobacterium/Rhizobium HSZ 30, Bacillus simplex K2, *Pseudomonas putida* K32, or Gordona sp. (DSM 19687), and with the functional equivalent variants and mutants thereof. These microorganisms are, as already described, deposited in accordance with the Budapest Treaty.

The microorganism species very particularly suitable for the process are Alcaligenes/Bordetella FB 188 (DSM 11172), *Rhodococcus erythropolis* CB 101 (DSM 10686) and Gordona sp. CB 100 (DSM 10687).

The biotransformation can be carried out, after conventional initial cultivation of these microorganisms, with quiescent cells (non-growing cells no longer requiring a carbon and energy source) or with growing cells. The biotransformation is preferably carried out with quiescent cells.

The enzymes according to the invention which are suitable for the process, the N-acetylamino-alcohol hydrolases, can be obtained by the methods described above and have the properties already described above.

Suitable penicillin G acylases are obtained from many microorganisms such as, for example, bacteria or actinomycetes, specifically from the following microorganisms: *Escherichia coli* ATCC 9637, *Bacillus megaterium*, *Streptomyces lavendulae* ATCC 13664, Nocardia sp. ATCC 13635, *Providencia rettgeri* ATCC 9918, *Arthrobacter viscosus* ATCC 15294, *Rhodococcus fascians* ATCC 12975, *Streptomyces phaeocliromogenes* ATCC 21289, Achromobacter ATCC 23584 and *Micrococcus roseus* ATCC 416. Penicillin G acylases which can be bought are used in particular, such as penicillin G acylase EC 3.5.1.11 from *E.coli* (Boehringer Mannheim) or from *Bacillus megaterium*.

Immobilized penicillin G acylases are used in a preferred embodiment.

The biotransformation can be carried out in media usual in the art, such as, for example, in low-molarity phosphate, citrate or Hepes buffer, in water, in complete media such as, for example, Nutrient Yeast Broth (NYB) or in that described in the table. The biotransformation is preferably carried out in the medium shown in Table 1 or in low-molarity phosphate buffer.

The biotransformation is expediently carried out with a single or continuous addition of the cyclopentene derivative (formula VII) so that the concentration does not exceed 10% by weight, preferably 2% by weight.

The pH during the biotransformation can be in a range from 5 to 9, preferably from 6 to 8. The biotransformation is expediently carried out at a temperature from 20 to 40° C., preferably from 25 to 30° C.

If the (1S,4R)-1-amino-4-(hydroxymethyl)-2-cyclopentene is formed during the biotransformation, this can be converted into the (1R,4S)-1-amino-4-(hydroxymethyl)-2-cyclopentene by acid hydrolysis, for example with hydrochloric acid.

EXAMPLES

Example 1

Preparation of (±)-2-Acetyl-2-azabicyclo [2.2.1] hept-5-en-3-one 100 g of (±)-2-azabicyclo[2.2.1]hept-5-en-3-one were dissolved in acetonitrile (800 ml) and pyridine (161.26 ml) under nitrogen. At 12° C., 104.5 g of acetyl chloride were added dropwise over the course of 2 hours. The mixture was then stirred at room temperature for 4.5 hours. 800 ml of water were added to the mixture, and the acetonitrile was evaporated off in vacuo. The aqueous phase was extracted 3 times with 400 ml of ethyl acetate. The combined org. phases were washed with 1N HCl (400 ml), water (400 ml), saturated NaCl (400 ml), dried with magnesium sulphate and completely evaporated. The residue was taken up in methylene chloride and filtered through silica gel. The filtrate was concentrated and the product was purified by distillation. 107.76 g of product were obtained as a clear liquid. The yield was 71%.

Boiling point (0.07 torr): 51° C.

| $^1$H—NMR (CDCl$_3$):δ[ppm] 400 MHz | 2.25 (AB syst., 2H); 2.8 (s, 3H); 3.42 (m, 1H); 5.30 (m, 1H); 6.89 (m, 1H); 6.92 (m, 1H). |
|---|---|

Example 2

Preparation of (±)-2-Butyryl-2-azabicyclo[2.2.1] hept-5-en-3-one 100.3 g of (±)-2-azabicyclo [2.2.1]hept-5-en-3-one were dissolved in acetonitrile (720 ml) and pyridine (142 ml) under nitrogen. At 12° C., 141.8 g of butyryl chloride were added dropwise over the course of 1 hour. The reaction was then stirred at room temperature for 3 hours. 720 ml of water were added to the mixture. The acetonitrile was evaporated off in vacuo, and the aqueous phase was extracted 3 times with ethyl acetate (300 ml). The combined org. phases were washed with 1N HCl (350 ml), saturated NaCl (400 ml) and water (500 ml), dried with magnesium sulphate and completely evaporated. The product was purified by distillation. 107.76 g of product were obtained as a clear liquid. The yield was 85%.

Boiling point (0.05 torr): 70° C.

| ¹H—NMR (CDCl₃):δ[ppm] | 0.98 (t, J = 8.5 Hz, 3H); |
|---|---|
| 400 MHz | 1.58–1.65 (2H); |
| | 2.23 (AB syst., 2H); |
| | 2.82–2.90 (2H); |
| | 3.42 (m, 1H); |
| | 5.30 (m, 1H); |
| | 6.62 (m, 1H); |
| | 6.90 (m, 1H). |

Example 3

Preparation of (±)-2-Phenylacetyl-2-azabicyclo[2.2.1]-hept-5-en-3-one 33.4 g of (±)-2-azabicyclo[2.2.1]hept-5-en-3-one were dissolved in acetonitrile (240 ml) and pyridine (48.3 ml) under nitrogen. At 12° C., 68.6 g of phenylacetyl chloride were added dropwise over the course of 30 minutes. The mixture was then stirred at room temperature for 3.5 hours. 240 ml of water were added to the mixture. The acetonitrile was evaporated off in vacuo and the aqueous phase was extracted 3 times with ethyl acetate (150 ml). The combined org. phases were washed with 1N HCl (150 ml), saturated NaCl (150 ml) and water (150 ml), dried with magnesium sulphate and completely evaporated. The crude product was filtered through silica gel (hexane:ethyl acetate=1:1). 68.34 g of the crude product were obtained as a yellow oil.

Example 4

Preparation of (±)-2-Propionyl-2-azabicyclo[2.2.1]hept-5-en-3-one 47 g of (±)-2-azabicyclo[2.2.1]hept-5-en-3-one were dissolved in acetonitrile (325 ml) and pyridine (41 ml) under nitrogen. At 12° C., 43.9 g of propionyl chloride were added dropwise over the course of 1 h. The reaction was then stirred at room temperature for 5 h. 145 ml of water were added to the mixture, and the acetonitrile was evaporated off in vacuo. The aqueous phase was extracted 3 times with 115 ml of ethyl acetate. The combined organic phases were washed with 1N HCl (140 ml), saturated NaHCO₃ (40 ml) and NaCl (40 ml) solutions, dried with sodium sulphate and completely evaporated. The residue was purified by distillation. 55.8 g of title compound were obtained and solidified on leaving to stand. The yield was 81.6%.

Boiling point 2.8 mbar 75–80° C.; Melting point: 54–56° C.

| ¹H—NMR (DMSO-d₆):δ[ppm] | 0.95 (t, 3H); |
|---|---|
| 400 MHz | 2.10 (quart., 1H); |
| | 2.28 (quart., 1H); |
| | 2.64 (m, 2H); |
| | 3.42 (s, 1H); |
| | 5.16 (s, 1H); |
| | 6.78 (m, 1H); |
| | 6.96 (m, 1H). |

Example 5

Preparation of (+)-2-Isobutyryl-2-azabicyclo[2.2.1]hept-5-en-3-one 45.1 g of (±)-2-azabicyclo[2.2.1]hept-5-en-3-one were dissolved in acetonitrile (310 ml) and pyridine (39 ml) under nitrogen. At 10° C., 54.1 g of isobutyryl chloride were added dropwise over the course of 1 h. The reaction was then stirred at room temperature for 5 h. 140 ml of water were added to the mixture, and the acetonitrile was evaporated off in vacuo. The aqueous phase was extracted with 4×120 ml of ethyl acetate. The combined organic phases were washed with 1N HCl (50 ml), saturated NaHCO₃ (50 ml) and NaCl (50 ml) solutions, dried with sodium sulphate and completely evaporated. The residue was boiled under reflux in n-hexane (240 ml) with active charcoal. After filtration of the active charcoal, the filtrate was cooled to 0° C. and the title compound was filtered. 54.5 g of product were obtained. The yield was 76 0.

Melting point: 41–42° C.

| ¹H—NMR (DMSO-d₆):δ[ppm] | 0.92 (d, 3H); |
|---|---|
| 400 MHz | 1.06 (d, 3H); |
| | 2.10 (m, 1H); |
| | 2.28 (m, 1H); |
| | 3.40 (m, 2H); |
| | 5.16 (s, 1H); |
| | 6.78 (m, 1H); |
| | 7.92 (m, 1H). |

Example 6

Preparation of (±)-2-Chloroacetyl-2-azabicyclo[2.2.1]-hept-5-en-3-one 10.1 g of (±)-2-azabicyclo[2.2.1]hept-5-en-3-one were dissolved in a mixture of dichloromethane (10 ml), pyridine (8.4 ml) and 0.22 g of 4-N,N-dimethylaminopyridine at 10° C. under nitrogen. 13.5 g of chloroacetyl chloride were added dropwise over the course of 1 h. The temperature rose to 44° C. The mixture was stirred for a further 2 h at room temperature. 100 ml of water were added to the solution. After phase separation, the aqueous phase was extracted with 100 ml of dichloromethane. The combined organic phases were dried with sodium sulphate and completely evaporated. The residue was boiled in 100 ml of diisopropyl ether under reflux in the presence of 1 g of active charcoal for 10 minutes. After hot filtration, the filtrate was cooled to room temperature, and the solid was filtered and dried. 10.35 g of title compound were obtained. The yield was 60 0.

Melting point: 86–88° C.

| ¹H—NMR (CDCl₃):δ[ppm] | 2.28 (d, 1H); |
|---|---|
| 400 MHz | 2.40 (d, 1H); |
| | 3.48 (s, 1H); |
| | 4.56 (d, 2H); |
| | 5.30 (s, 1H); |
| | 6.70 (d, 1H); |
| | 6.94 (m, 1H). |

Example 7

Preparation of (±)-1-Acetylamino-4-hydroxymethyl-2-cyclopentene 79.56 g of (±)-2-acetyl-2-azabicyclo[2.2.1]hept-5-en-3-one were dissolved in ethanol (450 ml) under nitrogen and cooled to –10° C. 19.8 g of sodium boro-hydride were added in portions over the course of 45 minutes.

The reaction was stirred at 0° C. for 3 hours and then the pH was adjusted to 1.8 with conc. sulphuric acid. Ethyl acetate (200 ml) was added to this mixture, and the solids were filtered off. It was then completely evaporated. The residue was taken up in water, washed with methylene chloride and completely evaporated. The crude product was purified by a silica gel filtration using ethyl acetate/methanol 5:1 as solvent. The filtrate was concentrated. 51.83 g of product were obtained as a white solid. The yield was 64% based on 2-acetyl-2-azabicyclo[2.2.1]hept-5-en-3-one employed.

Melting point 91–93° C.

| $^1$H—NMR (DMSO-d$_6$):δ[ppm] 400 MHz | 1.18 (m, 1H); 1.78 (s, 3H); 2.29 (m, 1H); 2.66 (m, 1H); 3.35 (s, 2H); 4.58 (s, 1H); 4.72 (m, 1H); 5.61 (d, 1H); 5.85 (d, 1H); 7.83 (d, 1H). |
|---|---|

Example 8

Preparation of (±)-1-Butyrylamino-4-hydroxymethyl-2-cyclopentene 73.87 g of (±)-2-butyryl-2-azabicyclo [2.2.1]hept-5-en-3-one were dissolved in ethanol (400 ml) under nitrogen and cooled to −10° C. 15.68 g of sodium boro-hydride were added in portions over the course of 45 minutes. The reaction was stirred at 0° C. for 3 hours and then the pH was adjusted to 1.5 with conc. sulphuric acid. Ethyl acetate (200 ml) was added to this mixture, and the solids were filtered off. It was then completely evaporated. The residue was taken up in water, washed with methylene chloride, evaporated and dried under high vacuum. 60.55 g of product were obtained. The yield was 80% based on (±)-2-butyryl-2-azabicyclo[2.2.1]hept-5-en-3-one employed.

Melting point 71–72° C.

| $^1$H—NMR (CDCl$_3$):δ[ppm] 400 MHz | 0.98 (t, J = 8.5 Hz, 3H); 1.40–1.50 (1H); 1.58–1.68(2H); 2.10–2.18(2H); 2.42–2.55 (1H); 2.85 (m, 1H); 3.62 (AB syst., 2H); 4.98 (m, 1H); 5.78–5.82 (2H); 6.38 (m, 1H). |
|---|---|

Example 9

Preparation of (±)-1-Phenylacetylamino-4-hydroxymethyl-2-cyclopentene 67 g of crude (±)-2-phenylacetyl-2-azabicyclo-[2.2.1]hept-5-en-3-one were dissolved in ethanol (450 ml) under nitrogen and cooled to −10° C. 13.2 g of sodium borohydride were added in portions over the course of 1 hour. The reaction was stirred at room temperature for 3.5 hours and then the pH was adjusted to 3.8 with conc. sulphuric acid. The mixture was completely evaporated. The residue was dried and purified by a silica gel filtration (hexane:ethyl acetate=1:9). After recrystallization from ethyl acetate, 54.6 g of white solid were obtained. The yield was 80% based on (±)-2-phenylacetyl-2-azabicyclo[2.2.1]hept-5-en-3-one employed.

| $^1$H—NMR (CDCl$_3$):δ[ppm] 400 MHz | 1.28–1.35 (1H); 1.40 (m, 1H); 2.38–2.45 (1H); 2.79 (m, 1H); 3.50 (AB syst., 2H); 3.52 (s, 3H); 4.98 (m, 1H); 5.75 (m, 2H); 5.98 (m, 1H). 7.20–7.38 (5H). |
|---|---|

Example 10

Preparation of (±)-1-BOC-amino-4-hydroxymethyl-2-cyclopentene 15 g of crude (±)-1-amino-4-hydroxymethyl-2-cyclopentene hydrochloride were dissolved in a mixture of 150 ml of water and 150 ml of dioxane at room temperature under nitrogen. The solution was adjusted to pH 14 with 1N NaOH, then a diethyl ether solution of tert-butyloxy-carbonyl fluoride (BOC-F, 20% excess) was added, and the mixture was stirred for a further 3 h at room temperature (BOC-F prepared as disclosed in Synthesis 1975, 599). The pH was adjusted to 2 with conc. HCl. After distillation of the organic solvents, 50 ml of water were added to the residue, and the mixture was extracted with 3×100 ml of ethyl acetate. The combined organic phases were completely evaporated. The residue was crystallized in a mixture of 110 ml of diisopropyl ether and 80 ml of n-hexane. 11.95 g of title compound were obtained. The yield was 56%.

Melting point: 68–70° C.

| $^1$H—NMR (DMSO-d$_6$):δ[ppm] 400 MHz | 1.18 (m, 1H); 1.38 (s, 9H); 2.26 (m, 1H); 2.65 (m, 1H); 3.33 (t, 2H); 4.45 (m, 1H); 4.55 (t, 1H); 5.62 (m, 1H); 5.79 (m, 1H); 6.73 (d, 1H). |
|---|---|

Example 11

Preparation of (±)-1-Propionylamino-4-hydroxymethyl-2-cyclopentene 16.6 g of (±)-2-propionyl-2-azabicyclo[2.2.1]-hept-5-en-3-one were dissolved in water (140 ml) and 2-butanol (66 ml) under nitrogen and cooled to −5° C. 3 g of sodium borohydride were added in portions over the course of 2 h. The mixture was stirred at 10° C. for 2.5 h and then adjusted to pH 2.2 with a mixture of conc. hydrochloric acid and water (1/1). The solution was evaporated to 40 g and adjusted to pH 6.2 with 2N NaOH. The mixture was extracted with 5×50 ml of dichloromethane. The combined organic phases were completely evaporated, and the residue was recrystallized in toluene (150 ml). 11.1 g of title compound were obtained. The yield was 65%.

Melting point: 67–68° C.

| $^1$H—NMR (DMSO-d$_6$):δ[ppm] 400 MHz | 0.96 (t, 3H); 1.16 (quint., 1H); 2.04 (quart., 2H); 2.26 (m, 1H); 2.66 (m, 1H); 3.34 (m, 2H); 4.58 (t, 1H); 4.72 (m, 1H); 5.61 (m, 1H), 5.84 (m, 1H), 7.72 (d, 1H). |
|---|---|

Example 12

Preparation of (±)-1-Isobutyrylamino-4-hydroxymethyl-2-cyclopentene 9 g of (±)-2-isobutyryl-2-azabicyclo[2.2.1]hept-5-en-3-one were dissolved in water (32 ml) and 2-butanol (84 ml) under nitrogen and cooled to 0° C. 1.37 g of sodium borohydride were added in portions over the course of 3.5 h. The mixture was stirred for a further 3 h at 20° C., and it was then adjusted to pH 2.5 with a mixture of conc. hydrochloric acid and water (1/1) and then neutralized with 2N NaOH. The solution was evaporated to 40 g. The residue was extracted with 3×80 ml of dichloromethane. The combined organic phases were completely evaporated. The resulting solid was crystallized in 25 ml of toluene. 6.8 g of title compound were obtained. The yield was 73.6%.

Melting point: 80–81° C.

| $^1$H—NMR (DMSO-d$_6$):δ[ppm] 400 MHz | 0.98 (d, 6H); 1.16 (quint., 1H); 2.30 (m, 2H); 2.68 (m, 1H); 3.32 (t, 2H); 4.58 (t, 1H); 4.70 (m, 1H); 5.61 (m, 1H); 5.82 (m, 1H); 7.68 (d, 1H). |
|---|---|

Example 13

Preparation of (1R,4S)-1-Amino-4-(hydroxymethyl)-2-cyclopentene Using Penicillin G Acylases Penicillin G acylase EC 3.5.1.11 from *E.coli* (Boehringer Mannheim) 165 U (units)/g or penicillin G acylase EC 3.5.1.11 from *Bacillus megaterium* was employed for the biotransformation.

For this, 50 mM sodium phosphate buffer (pH 5–9; 4 ml) was incubated with to by weight of non-racemic 1-phenylacetylamino-4-hydroxymethyl-2-cyclopentene and 400 mg of the appropriate penicillin G acylase at 37° C.

Samples were taken after defined time intervals and were analyzed by thin-layer chromatography (silica gel 60, butanol:water:glacial acetic acid=3:1:1; detection with ninhydrin), gas chromatography (capillary column, HP-5, 5% phenylmethylsiloxane) or HPLC. The enzyme eliminated the phenylacetyl group with high activity and thereby liberated up to 40% of the corresponding amino alcohol. The free amino alcohol was obtained with a ee of 80%.

Example 14

Preparation of (1R,4S)-1-Amino-4-(hydroxymethyl)-2-cyclopentene Using Microorganisms 14.1 Sewage sludge (200) from the ARA water treatment plant in Visp was incubated in the A+N medium (see Table 1) containing 0.5% by weight of 1-acetyl-, 1-propionyl-, 1-isobutyryl- or 1-butyrylamino-4-hydroxymethyl-2-cyclopentene at 37° C. with shaking. The formation of (1R,4S)-1-amino-4-(hydroxymethyl)-2-cyclopentene was followed by thin-layer chromatography.

1–3 transfers were carried out with to of these enrichments, and isolation took place on solid media (plate count agar in the medium of Table 1; 20 g/l). The microorganisms Alcaligenes/Bordetella FB 188 (DSM 1172), *Rhodococcus erythropolis* CB 101 (DSM 10686), Gordona sp. CB 100 (DSM 10687) and Rhodococcus sp. FB 387 (DSM 11291) were isolated in this way.

14.2 The microorganisms isolated in this way were cultivated in the medium (Table 1) containing 0.50 of 1-acetyl-, 1-propionyl-, 1-isobutyryl- or 1-butyryl-amino-4-hydroxymethyl-2-cyclopentene. They grew to an optical density (OD) of 2 to 3 in 24 to 36 hours. The cells obtained in this way were harvested in the late exponential phase of growth and were washed in 10 mM phosphate buffer.

The subsequent biotransformation was carried out in 50 mM phosphate buffer (pH 4.5–9) containing to by weight of 1-acetyl-, 1-isobutyryl- or 1-butyrylamino-4-hydroxymethyl-2-cyclopentene. It was found by thin-layer chromatography that 50% of the substrate were hydrolyzed to (1R,4S)-1-amino-4-(hydroxymethyl)-2-cyclopentene. HPLC analyses revealed ee values between 80 and 93%.

When 1-butyrylamino-4-hydroxymethyl-2-cyclopentene was employed as substrate, the biotransformation rate was 0.14 (g/l/h/OD) for the strain DSM 10686 when cultivation took place on a A+N medium and 0.03 (g/l/h/OD) when cultivation took place on NYB (nutrient yeast broth) medium containing 1-butyrylamino-4-hydroxymethyl-2-cyclopentene.

When the same conversion was carried out with the strain DSM 10687 at a substrate concentration (1-butyrylamino-4-hydroxymethyl-2-cyclopentene) of 200 mM, the biotransformation rate was 0.161 (g/l/h/OD).

TABLE 1

| A + N medium | |
|---|---|
| MgCl$_2$ | 0.4 g/l |
| CaCl$_2$ | 0.014 g/l |
| FeCl$_3$ | 0.8 mg/l |
| Na$_2$SO$_4$ | 0.1 g/l |
| KH$_2$PO$_4$ | 1 g/l |
| Na$_2$HPO$_4$ | 2.5 g/l |
| NaCl | 3 g/l |
| Vitamin solution | 1 ml/l |
| Trace element solution | 1 ml/l |
| pH | 7.5 |

14.3 *Rhodococcus erythropolis* DSM 10686 was cultured in minimal medium (cf. Table 2) with ammonium acetate (3 g/l) as carbon and nitrogen source in a 6 l fermenter at 30° C. to a cell density of OD 650>25. During cell growth, 50% acetic acid was added con-tinuously as additional C. source. In order to induce the enzymatic activity, 60 g of (+/−)-1-acetylamino-4-hydroxymethyl-2-cyclopentene were then added, and incubation was continued for some hours.

Finally, a further 40 g of (+/−)-1-acetylamino-4-hydroxymethyl-2-cyclopentene were added, and incubation was then carried out for a further 10 hours. The progress of the biotransformation was followed on-line by HPLC. When an analytical yield of 40%, based on the racemic substrate employed, and a ee of 85% were reached, fermentation was stopped by adding acid.

TABLE 2

Media composition

| Component | Concentration |
|---|---|
| Yeast extract | 0.5 g/l |
| Peptone M66 | 0.5 g/l |
| $KH_2PO_4$ | 4.0 g/l |
| $Na_2HPO_4 2H_2O$ | 0.5 g/l |
| $K_2SO_4$ | 2.0 g/l |
| $NH_4$ acetate | 3.0 g/l |
| $CaCl_2$ | 0.2 g/l |
| $MgCl_2 \cdot 6H_2O$ | 1.0 g/l |
| Trace element solution (see below) | 1.5 ml/l |
| PPG (polypropylene glycol) | 0.1 g/l |

| Trace element solution | |
|---|---|
| KOH | 15.1 g/l |
| $EDTA \cdot Na_2 \cdot 2 H_2O$ | 100.0 g/l |
| $ZnSO_4 \cdot 7H_2O$ | 9.0 g/l |
| $MnCl_2 \cdot 4H_2O$ | 4.0 g/l |
| $H_3BO_3$ | 2.7 g/l |
| $COCl_2 \cdot 6H_2O$ | 1.8 g/l |
| $CUCl_2 \cdot 2H_2O$ | 1.5 g/l |
| $NiCl_2 \cdot 6H_2O$ | 0.18 g/l |
| $Na_2MoO_4 \cdot 2H_2O$ | 0.27 g/l |

14.4 In analogy to Example 14.3, the microorganisms Arthrobacter sp. HSZ 5 (DSM 10328, Rhodococcus sp. FB387 (DSM 11291), Alcaligenes xylosoxydans ssp. denitrificans HSZ 17 (DSM 10329), Agrobacterium/Rhizobium HSZ 30, Bacillus simplex K2 and Pscudomonas putida K32 were cultured on sodium acetate in the medium (Table 1) with and without 1-acetyl-, 1-propionyl-, 1-isobutyryl- or 1-butyrylamino-4-hydroxymethyl-2-cyclopentene, abbreviated to amino alcohols hereinafter.

The following results were obtained with exponential cells cultured without amino alcohols (HPLC analysis)

| Strain | Rate [mmol/OD.h] | ee/conversion [%] |
|---|---|---|
| HSZ 5 (DSM 10328) | 0.05 | 88.7/16 |
| HSZ 17 (DSM 10329) | 0.005 | 95/23 |
| K32 | 0.05 | 54/1 |
| CB101 (DSM 10686) | 0.1 | 84/39 |

The strains K2 and K17 were cultured, harvested and subjected to a 60-hour biotransformation.

| Strain | Rate [mmol/OD.h] | ee/conversion [%] |
|---|---|---|
| K2 | — | 92/10 |
| HSZ 30 | — | 93/3.5 |

Exponential and stationary cells were harvested from all the batches and employed as quiescent cells for the biotransformation. There was no observable difference, from the TLC analysis, in the initial rate of cells induced with amino alcohol or not induced.

Example 15

Purification of the N-acetylamino-alcohol Hydrolase from Rhodococcus Erythropolis CB101 (DSM 10686)

The enzyme was purified as described below until there was only one protein band in the SDS-PAGE (Pharmacia Phast gel, 10–15o gradient) at a molecular weight of 50 kD.

Cells of Rhodococcus erythropolis CB101 (DSM 10686) were washed in 50 mM tris buffer (pH 6.2) and concentrated to an optical density $OD_{650nm}$ of 190. After addition of phenylmethanesulphonyl fluoride (PMSF) to a final concentration of 1 mM and DNAse, the cells were treated with a French press in order to obtain a crude extract. Centrifugation resulted in 200 ml of a cell-free extract with a protein concentration of 4.8 mg $ml^{-1}$.

960 mg of the cell-free extract were loaded onto a HiLoad 26/10 Q-Sepharose ion exchange chromatography column (Pharmacia) which had been equilibrated with a 50 mM tris buffer (pH 8.0) containing 1 mM dithiothreitol (DTT).

After the column had been washed with the same buffer, the proteins were eluted with a linear buffer gradient (1500 ml, gradient: 50 mM tris buffer (pH 8.0) containing 1 mM DTT—50 mM tris buffer (pH 7.0) containing 1 mM DTT and 1 M NaCl). The enzyme eluted from the column between 370 and 430 mM NaCl and at a pH of 7.6. The active fractions were collected and concentrated to 9 ml. The protein content was 41 mg.

For further purification, the protein solution was loaded onto a HiLoad 26/60 Superdex 75 gel filtration chromatography column (Pharmacia) which had been equilibrated with a 50 mM tris buffer containing 50 mM NaCl and 1 mM DTT. The active fractions were combined and had a total protein content of 10.9 mg.

This protein solution was loaded onto a Mono Q HR5/5 column (Pharmacia) which had been equilibrated with 50 mM tris buffer (pH 8.5) containing 1 mM DTT. The proteins were eluted with a linear gradient (40 ml) of 50 mM tris buffer (pH 8.5) containing 1 mM DTT—50 mM tris buffer (pH 8.5) containing 1 mM DTT and 1 M NaCl. The enzyme eluted between 390 mM NaCl and 440 mM NaCl. The active fractions contained 1.4 mg of protein.

In the last purification step, the same column was used, equilibrated with the same buffer. The elution gradient used was the same buffer with 0–500 mM NaCl and pH 7.0–8.5. It was possible in this way to isolate 430 μg of pure enzyme.

The N-terminal sequence of the enzyme was determined directly from the protein blot. A sequence of the following 20 amino acids was obtained: Thr-Glu-Gln-Asn-Leu-His-Trp-Leu-Ser-Ala-Thr-Glu-Mct-Ala-Ala-Ser-Val-Ala-Ser-Asn.

This sequence showed no homology with known proteins.

Example 16

Enzyme Characterization

The enzyme characterization was carried out both with purified enzyme and with cell-free extract which had been desalted using a Sephadex G-25 column (PD-10, Pharmacia).

The protein concentration in the cell-free extract was 7.3 mg $ml^{-1}$ and the protein concentration of the purified enzyme was 135 μg ml$^{-1}$. PMSF was not added to the cell-free extract.

16.1 $K_m$ determination

The $K_m$ determination was carried out in a cell-free extract. The $K_m$ for the reaction at pH 7.0 and at a temperature of 30° C. was 22.5 mM for the substrate 1-acetylamino-4-hydroxymethyl-2-cyclopentene.

16.2 pH optimum

The pH optimum for the hydrolysis of 1-acetylamino-4-hydroxymethyl-2-cyclopentene (25 mM) was determined with the purified enzyme and in cell-free extract in a pH range of pH 6.2–9.0 in the following buffer solutions.

Tris buffer 100 mM pH 9.0; 8.5; 8.0; 7.5; 7.0

Citrate/phosphate buffer 100 mM pH 7.0; 6.55; 6.2

The activity was measured for 24 h.

The pH optimum for the reaction was between pH 7.0 and pH 7.5 for production of the 1R,4S and the 1S,4R enantiomer.

The pH optimum for the activity in the cell-free extract was at pH 7.0. The selectivity was, however better between pH 6.0 and pH 7.0.

What is claimed is:

1. A process for the preparation of (1R,4S)- or (1S,4R)1-amino-4-(hydroxymethyl)-2-cyclopentene of formula I and II:

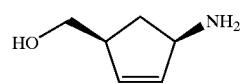

I

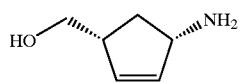

II or of (1S,4R)- or (1R,4S)-amino alcohol dereivatives of the general formula III and IV.

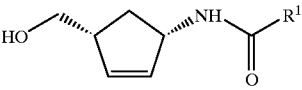

III

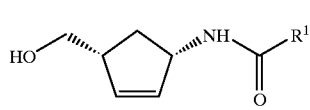

IV in which R1 denotes $C_1$–$C_4$-alkyl-, $C_1$–$C_4$-alkoxy, aryl, or aryloxy, comprising:

(i) the conversion of a cyclopentene derivative of the general formula:

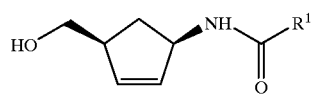

in which R1 denotes $C_1$–$C_4$-alkyl, $C_1$–$C_4$-alkoxy, aryl, or aryloxy, using (a) a microorganism that is able to utilize cyclopentene derivatives selected from the group of compounds of the general formula:

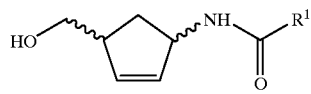

VII wherein R1 denotes $C_1$–$C_4$-alkyl, $C_1$–$C_4$-alkoxy, aryl, or aryloxy, as sole nitrogen source, as sole carbon source or as sole carbon and nitrogen source, and enzyme extracts thereof, or (b) an enzyme having N-acetylamino-alcohol hydrolase activity, obtainable from the microorganism of step (a) wherein said microorganism is able to hydrolyse cyclopentene derivatives selected from compounds of the general formula:

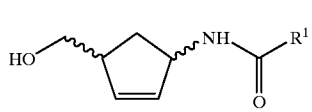

VII

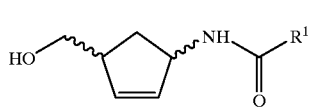

VII wherein R1 denotes $C_1$–$C_4$-alkyl, $C_1$–$C_4$-alkoxy, aryl, or aryloxy, and functionally equivalent variants and mutants thereof; or (c) penicillin G acylase;

into the compounds of the formula I or II or amino alcohol derivatives of the formula III or IV; and (ii) where appropiate, isolation of the compounds or the amino alcohol derivatives of the compounds resulting from the conversion.

2. The process according to claim 1, in which the cyclopentene derivative is of the general formula:

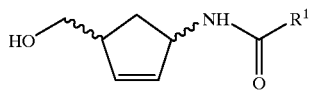

VII wherein R1 denotes $C_1$–$C_4$-alkyl, $C_1$–$C_4$-alkoxy, aryl or aryloxy, is prepared using a method comprising:

(i) acylating (±)-2-azabicyclo[2.2.1]hept-5-en-3-one-of the formula:

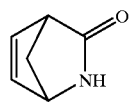

to give a (±)-2-azabicyclo[2.2.1]hept-5-en-3-one-of the formula:

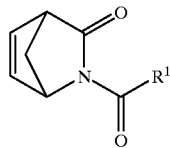

in which R1 denotes $C_1$–$C_4$-alkyl, $C_1$–$C_4$-alkoxy, aryl or aryloxy, and:

(ii) reducing this compound to a cyclopentene derivative of the general formula III.

3. The process of claim 2, wherein the acylation is carried out with a carbonyl halide of the general formula:

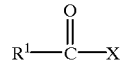

VIII in which X denotes a halogen atom, and R1 denotes $C_1$–$C_4$-alkyl, $C_1$–$C_4$-alkoxy, aryl or aryloxy, or with a carboxylic anhydride of the general formula:

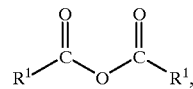

IX wherein R1 denotes $C_1$–$C_4$-alkyl, $C_1$–$C_4$-alkoxy, aryl or aryloxyloxy.

4. The process according to claim 2 wherein the acylation in step (i) is carried out in an aprotic solvent.

5. The process according to claim 2 wherein the reduction in step (ii) is carried out with an alkali metal or alkaline earth metal borohydride, an alkali metal or alkaline earth metal aluminum hydride and/or with Vitride.

6. The process according to claim 2 wherein the reduction in step (ii) is carried out in a protic solvent.

7. The process according to claim 1 wherein the conversion of the cyclopentene derivative of step (i) is carried out using a microorganism selected from the group consisting of the genera Rhodococcus, Gordona, Arthrobacter, Alcaligenes, Agrobacterium/Rhizobium, Bacillus, Pseudomonas or Alcaligenes/ Bordetella.

8. The process according to claim 1 wherein the conversion of the cyclopentene derivative of step (i) is carried out using penicillin G acylase derived from *Bacillus megaterium* or *Escherichia coli*.

9. The process according to claim 1 wherein conversion of the cyclopentene derivative is carried out at a temperature from 20° to 40° C. and a pH range from 5 to 9.

10. The process according to claim 1 wherein the enzyme having N-acetylamino-alcohol hydrolase activity is further characterized by having:

(a) a pH optimum of pH 7.0±1.0;

(b) a temperature optimum between 25° C. and 30° C. at a pH of 7.0; and (c) a $K_m$ for the substrate 1-acetylamino-4-hydroxy-methyl-2-cyclopentene of 22.5 mM±7.5 mM at 30° C. in 100 mM phosphate buffer.

11. The process of claim 1 wherein the microorganism is selected from the group consisting of the genus Rhodocaccus, Gordana, Arthrobacter, Alcaligenes, Agrobacterium/Rhizobium, Bacillus, Pseudomonas, or Alcaligenes/Bordetella.

12. The process of claim 1 wherein the microorganism is selected from the group consisting of Alcaligenes/Bordetella FB 188, *Rhodococcus erthropolis* CB 101, Arthrobacter sp. HS7.5, Rhodococcus sp. FB 387, *Alcaligenes xylosoxydans* ssp. *denitrificans* HSZ 17, Agrobacterium/Rhizobium IISZ 30, *Bacillus simplex* K2, *Pseudomonas pultilda* K32, or Gordona sp. CB100.

13. The process of claim 1 wherein the microorganism is selected from the group consisting of Alcaligenes/Bordetella FB 188 (DSM 11172), *Rhodococcus erthropolis* CB 101 (DSM 10686), Arthrobacter sp. HSZ 5 (DSM 10328), Rhodacoccus sp. FB 387 (DSM 11291), *Alcaligenes xylosoxydans* ssp. *denitrificans* HSZ 17 (DSM 10329), or Gordona sp. CB 100 (DSM 10687).

* * * * *

UNITED STATES PATENT AND TRADEMARK OFFICE
CERTIFICATE OF CORRECTION

PATENT NO. : 6,368,850 B1
DATED : April 9, 2002
INVENTOR(S) : Bernegger-Egli et al.

It is certified that error appears in the above-identified patent and that said Letters Patent is hereby corrected as shown below:

Title page,
Item [56], References Cited, OTHER PUBLICATIONS, under Martinez, et al., reference "carbocylic" should read -- carbocyclic --

Item [57], ABSTRACT, formula VII:

Column 1,
Line 18, "(1R4S)" should read -- (1R,4S) --
Formula VII:

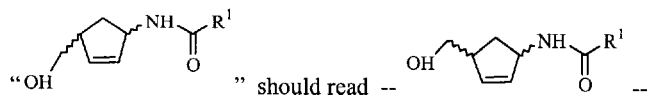

Line 53, "(ibid)" should read -- (ibid.) --
Line 53, "Park, K. II." should read -- Park, K. H. --

Column 2,
Line 37, "*crythropolis*" should read -- *erythropolis* --
Lines 39-40, "16.3 The temperature optimum for the reaction indicated in Example 16.2 was between 25 and 30° C." should be deleted
Line 41, "N-acctylaminoalcohol" should read -- N-acetylamino-alcohol --
Formula VII:

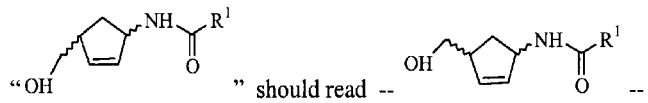

Column 3,
Line 38, "takes" should read -- take --
Line 43, "genus" should read -- genera --
Line 63, "mean" should read -- means --

UNITED STATES PATENT AND TRADEMARK OFFICE
CERTIFICATE OF CORRECTION

PATENT NO. : 6,368,850 B1
DATED : April 9, 2002
INVENTOR(S) : Bernegger-Egli et al.

It is certified that error appears in the above-identified patent and that said Letters Patent is hereby corrected as shown below:

Column 4,
Line 27, "*Erythropolis*" should read -- *erythropolis* --

Column 5,
Line 51, "Axthrobacter" should read -- Arthrobacter --
Line 61, "Peptidoglkycan" should read -- Peptidoglycan --
Line 61, "A3cx" should read -- A3α --

Column 8,
Line 44, "KM" should read -- $K_M$ --

Column 10,
Formula VII:

Column 11,
Line 28, "Algaligenes" should read -- Alcaligenes --
Line 58, "*phaeocliromogenes*" should read -- *phaeochromogenes* --

Column 18,
Line 13, "to" should read -- 1% --
Line 64, "con-tinuously" should read -- continuously --

Column 19,
Line 32, "COCl$_2$" should read -- CoCl$_2$ --
Line 33, "CUCl$_2$" should read -- CuCl$_2$ --
Line 40, "*Pscudomonas*" should read -- *Pseudomonas* --

Column 21,
Line 43, "(1S, 4R)1-" should read -- (1S, 4R)-1- --
Line 59, "dereivatives" should read -- derivaties --

UNITED STATES PATENT AND TRADEMARK OFFICE
CERTIFICATE OF CORRECTION

PATENT NO.   : 6,368,850 B1
DATED        : April 9, 2002
INVENTOR(S)  : Bernegger-Egli et al.

It is certified that error appears in the above-identified patent and that said Letters Patent is hereby corrected as shown below:

Column 22,
Line 56, "hydrolyse" should read -- hydrolyse --

Column 23,
Line 5, "appropiate" should read -- appropriate --
Line 20, "hept-5-en-3-one-of" should read -- hept-5-en-3-one of --
Line 29, "-one-of" should read -- one of --
Line 41, "aryloxy, and:" should read -- aryloxy; and --

Column 24,
Line 8, "aryloxyoxy" should read -- aryloxy --
Lines 19-21, "Rhodococcus, Gordona, Arthrobacter, Alcaligenes, Agrobacterium/Rhizobium, Bacillus, Pseudomonas or Alcaligenes/ Bordetella." should read -- *Rhodococcus, Gordona, Arthrobacter, Alcaligenes, Agrobacterium/Rhizobium, Bacillus, Pseudomonas* or *Alcaligenes/ Bordetella.* --
Line 38, "genus" should read -- genera --
Line 39, "Rhodocaccus," should read -- *Rhodococcus,* --; and "Gordana" should read -- *Gordona* --
Lines 38-40, "Arthrobacter, Alcaligenes, Agrobacterium/Rhizobium, Bacillus, Pseudomonas, or Alcaligenes/Bordetella." should read -- *Arthrobacter, Alcaligenes, Agrobacterium/Rhizobium, Bacillus, Pseudomonas,* or *Alcaligenes/Bordetella.* --
Line 42, "Alcaligenes/Bordetella" should read -- *Alcaligenes/Bordetella* --
Line 43, "*Rhodacoccus*" should read -- *Rhodococcus* --; and "*erthropolis*" should read -- *erythropolis* --
Line 43, "Arthrobacter sp." should read -- *Arthrobacter sp.* --
Line 44, "HS7.5" should read -- HSZ 5 --
Line 45, "ssp." should read -- *ssp.* --
Line 45, "Agrobacterium/Rhizobium" should read -- *Agrobacterium/Rhizobium* --; and "IISZ" should read -- HSZ --
Line 47, "Gordona sp." should read -- *Gordona sp.* --
Line 49, "Alcaligenes/Bordetella" should read -- *Alcaligenes/Bordetella* --
Line 50, "*Rhodacoccus*" should read -- *Rhodococcus* --; and "*erthropolis*" should read -- *erythropolis* --
Line 51, "Arthrobacter sp." should read -- *Arthrobacter sp.* --
Lines 51-52, "Rhodacoccus sp." should read -- *Rhodococcus sp.* --

UNITED STATES PATENT AND TRADEMARK OFFICE
CERTIFICATE OF CORRECTION

PATENT NO.   : 6,368,850 B1
DATED        : April 9, 2002
INVENTOR(S)  : Bernegger-Egli et al.

It is certified that error appears in the above-identified patent and that said Letters Patent is hereby corrected as shown below:

<u>Column 24 cont'd,</u>
Line 53, "ssp." should read -- *ssp.* --
Line 54, "Gordona" should read -- *Gordona* --
Line 55, "sp." should read -- *sp.* --

Signed and Sealed this

Fourth Day of February, 2003

JAMES E. ROGAN
*Director of the United States Patent and Trademark Office*